United States Patent [19]

Mitchell

[11] Patent Number: 4,521,608
[45] Date of Patent: Jun. 4, 1985

[54] SEPARATION OF 1,8-CINEOLE BY FORMING A COMPLEX WITH HYDROQUINONE

[75] Inventor: Peter W. D. Mitchell, Freehold, N.J.

[73] Assignee: Union Camp Corporation, Wayne, N.J.

[21] Appl. No.: 494,108

[22] Filed: May 12, 1983

[51] Int. Cl.$^3$ ............................................. C07D 311/02
[52] U.S. Cl. ..................................... 549/397; 549/463
[58] Field of Search ................................ 549/397, 463

[56] References Cited

U.S. PATENT DOCUMENTS

| | | | |
|---|---|---|---|
| 2,090,620 | 9/1936 | Bibb | 549/397 |
| 2,315,986 | 4/1943 | Scrutchfield | 549/397 |
| 3,923,837 | 12/1975 | Davis | 549/397 |
| 4,347,189 | 8/1982 | Goldstein | 549/397 |

Primary Examiner—Nicky Chan
Attorney, Agent, or Firm—Kane, Dalsimer, Kane, Sullivan and Kurucz

[57] ABSTRACT

Mixtures containing 1,8-cineole are treated with hydroquinone to complex with and precipitate the 1,8-cineole. The complex in a crystalline form is separated from the mixture and dissociated to give 1,8-cineole which may be isolated in high-purity form by filtration or distillation.

7 Claims, No Drawings

SEPARATION OF 1,8-CINEOLE BY FORMING A COMPLEX WITH HYDROQUINONE

BACKGROUND OF THE INVENTION

Field of the Invention

The invention relates to the separation of 1,8-cineole from mixtures with 1,4-cineole and/or terpene hydrocarbons.

BRIEF DESCRIPTION OF THE INVENTION

The compound 1,8-cineole (eucalyptol) occurs in a very large number of naturally-derived essential oils and finds wide use as a flavorant in beverages, ice cream, baked goods and chewing gum and as a fragrance ingredient in medicinal products. In certain commercial chemical processes 1,8-cineole is co-produced in admixture with its isomer, 1,4-cineole(1,4-epoxy-p-menthane) and with various terpene hydrocarbons. For example, both cineoles are found in the mixture of by-product terpenes called "pine oil dipentene", which is produced during hydration of alpha-pinene or dehydration of terpin hydrate.

The structural formulae of the cineole isomers are as follows:

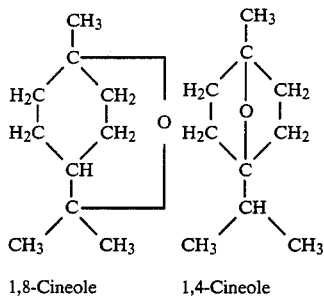

1,8-Cineole        1,4-Cineole

The presence of 1,4-cineole and of terpene hydrocarbons is detrimental to the majority of the uses of 1,8-cineole. It is, therefore, desirable to isolate the 1,8-isomer from the 1,4-isomer and from associated terpene hydrocarbons. A number of separation procedures have been described in the prior art literature. Representative of those descriptions are those found in the U.S. Pat. Nos. 2,090,620; 2,315,986; 2,353,319; 2,459,432; 2,459,433 and 4,347,189 and German Patentschrift No. 585,162 issued Sept. 29, 1933.

The present invention is an improved method of separating 1,8-cineole in relatively pure form from 1,4-cineole and terpene hydrocarbons. The method of the invention has a number of advantages over prior art methods. For example, the agent used to complex with and separate the 1,8-cineole is hydroquinone, an inexpensive and widely used industrial chemical. Hydroquinone, unlike resorcinol, o-cresol and other phenolic agents used in prior art methods, is insoluble in terpene hydrocarbons and can, therefore, be recovered in pure form and re-used without loss by simple filtration, extraction or distillation techniques. The terpene hydrocarbons from which the 1,8-cineole is separated are also readily recovered and require no extensive treatment for the removal of dissolved phenol for their further use or sale. The advantage is an economic one. The method of the invention may also be carried out using a column packed with the hydroquinone, allowing the process to be carried out in a semi-continuous manner assuring a uniform, high-quality product without the need to handle the separating agent.

SUMMARY OF THE INVENTION

The invention comprises a method of separating 1,8-cineole from mixtures of said 1,8-cineole with 1,4-cineole and/or terpene hydrocarbons, which comprises; reacting the 1,8-cineole with hydroquinone to form a complex which is insoluble in said mixture; separating the insoluble complex, and dissociating the separated complex to recover the 1,8-cineole.

DETAILED DESCRIPTION OF THE PREFERRED EMBODIMENT OF THE INVENTION 1,8-Cineole and, to a much lesser extent, 1,4-cineole react with hydroquinone to form addition complexes consisting of up to two cineole molecules bound to one molecule of hydroquinone. For example, the complex resulting from the reaction of 2 moles of 1,8-cineole and 1 mole of hydroquinone is a crystalline solid with a melting point of about 75° C. which is insoluble in water and hydrocarbon solvents. In contrast, the 1,4-isomer does not form a crystalline solid complex with hydroquinone.

In its simplest aspect, the method of the invention may be carried out by admixing a stoichiometric excess of hydroquinone with 1,8-cineole-containing mixture under conditions whereby the crystalline form of the 1,8-cineole/hydroquinone complex will form and precipitate. The precipitate may be separated from the mixture and dissociated to yield the 1,8-cineole and hydroquinone which are separable by distillation, solvent extraction or filtration.

In one embodiment of the method of the invention, the hydroquinone will be introduced into the mixture containing the 1,8-cineole as an aqueous solution of up to 5 percent concentration. In a preferred embodiment, anhydrous hydroquinone is employed instead of an aqueous solution thereof to obtain improved yields and purity of product 1,8-cineole.

The temperature at which the method of the invention is carried out should be such that the crystalline form of the reaction product of the 1,8-cineole and the hydroquinone is produced in the reaction mixture. When the mixture from which the 1,8-cineole is to be separated includes terpene hydrocarbons, the temperature is generally within the range of from about −30° C. to 30° C.

The purity of the separated 1,8-cineole may be further improved by re-complexation with hydroquinone or by subsequent recrystallizations from solvents such as aqueous acetone, aqueous alcohol, and the like, employing conventional recrystallization techniques.

The method of the invention may be carried out in batch or semi-continuous separations. In a preferred embodiment method of the invention, a semi-continuous process may be used, by passing the 1,8-cineole-containing mixture through a column containing hydroquinone. The complex of 1,8-cineole is formed on the surface of the hydroquinone and retained on the column. Means may be advantageously used to cool the column during passage of the mixture for separation. The complex of 1,8-cineole and hydroquinone may then be removed from the surface of the solid hydroquinone by dissociation of the complex (advantageously by passage of warm solvent such as heptane, toluene or the like)

and elution of the 1,8-cineole in the solvent. Simple evaporation or distillation of the solvent will allow recovery of the desired 1,8-cineole from the elute.

The following examples describe the manner and the process of making and using the invention and set forth the best mode contemplated by the inventor for carrying out the invention but are not to be construed as limiting. The feedstock for these examples was obtained by the fractional distillation of pine oil dipentene and is referred to as "Unitene-D" (Union Camp Corp). It analyzed as 18 weight % 1,8-cineole, 20 weight % 1,4-cineole and 55 weight % monocyclic terpene hydrocarbons.

EXAMPLE 1

Unitene-D (500 g) was stirred with a 4.5 weight % solution of hydroquinone in water (1.1 kg) at 3° C. for 1 hour. The crystalline precipitate which appeared in the organic phase was removed by filtration (73 g) and analyzed to contain 1,8-cineole, 1,4-cineole and other terpenes in the relative amounts of 88%, 7%, and 5%. This solid was further purified by stirring it (46 g) with heptane (50 g) and water (100 g) at 50° C. until dissociation of the complex was complete and then cooling the mixture to 3° C. for 1 hour to re-precipitate the complex in the heptane phase. The solid was removed by filtration (34 g) and treated with steam to dissociate the complex, regenerate aqueous hydroquinone and distill product 1,8-cineole of 98.1% purity.

EXAMPLE 2

Unitene-D (1.0 kg) and anhydrous hydroquinone (200 g) was stirred at −10° C. for 3 hours. The mixture was filtered and the recovered solid cake washed three times with cold (−10° C.) heptane (250 g portions). Combined spent filtrate contained on the order of only 0.1% hydroquinone. Product was then obtained by washing the cake with warm (60° C.) heptane three times (250 g portions) and distilling the combined filtrates. The remaining solid in the solvent-wet cake was found to be pure hydroquinone. This was returned to the reactor for re-use. A typical run yields 88 g of product oil containing 95.1% 1,8-cineole. This represents 47% of the 1,8-cineole present in the feedstock. There is no difference in product yield or purity if recycled hydroquinone is used.

EXAMPLE 3

A distillation flask was charged with Unitene-D (29 g) and hydroquinone (10 g), cooled on an ice-water bath and the volatile materials removed under high vacuum. The flask contents were then warmed to 50° C. to distill 1,8-cineole product (2.8 g) of 96.1% purity. This represents 52% of the 1,8-cineole present in the feedstock mixture.

EXAMPLE 4

Crystalline anhydrous hydroquinone (19.5 g) was added to a 1 cm diameter jacketed glass chromatography column filled with heptane. The heptane was then drained to the level of the top of the packed hydroquinone, cold acetone poured into the jacket to chill the column contents below −10° C., and Unitene-D (20 g) added. The column contents were then eluted with heptane (about 250 ml) with continued chilling over 2 hours. This removed most of the undesirable components of the feed. The jacket was then drained of coolant and the column warmed to room temperature. Continued elution with heptane provided a solution of 1,8-cineole (1.8 g) of 92.8% purity (solvent-free basis). This represents a 50% yield of 1,8-cineole present in the feedstock mixture.

EXAMPLE 5

A mixture of 18 g of Unitene-D and 3.6 g of hydroquinone was stirred for 17 hours at 30° C. The mixture was filtered and the complex washed with pentane and air-dried. It weighed 3.84 g and analyzed (wt %), 19.51% 1.8-cineole and 0.159% 1,4-cineole. This represents a purity of 99.2% and a recovery of 22.4% of the 1,8-cineole contained in Unitene-D.

What is claimed:

1. A method of separating 1,8-cineole from mixtures of said 1,8-cineole with 1,4-cineole and terpene hydrocarbons, which comprises; reacting the 1,8-cineole with solid anhydrous hydroquinone to form a crystalline complex which is insoluble in said mixture; separating the insoluble complex; and dissociating the separated complex to recover the 1,8-cineole.

2. The method of claim 1 wherein the mixture is a mixture of cineoles and monocyclic terpenes obtained as a by-product of the hydration of alpha-pinene.

3. The method of claim 1 wherein the complex is dissociated, recrystallized, separated from the mother liquor and steam distilled to recover the 1,8-cineole.

4. The method of claim 1 wherein the complex is dissociated by contacting it with a hydrocarbon solvent and the mixture filtered to give separately a solution of 1,8-cineole and hydroquinone.

5. The method of claim 1 wherein the complex is formed at a temperature within the range of from −30° C. to 60° C.

6. The method of claim 1 wherein the complex is formed at a temperature within the range from −20° C. to +10° C.

7. The method of claim 1 wherein the hydroquinone is in the form of a solid column.

* * * * *